US00PP11606P

United States Patent [19]

Boeder

[11] Patent Number: Plant 11,606

[45] Date of Patent: Oct. 31, 2000

[54] CHRYSANTHEMUM PLANT NAMED 'GOLD CREST'

[75] Inventor: Mark Boeder, West Wittering, United Kingdom

[73] Assignee: Cleangro Limited, United Kingdom

[21] Appl. No.: 09/167,076

[22] Filed: Oct. 6, 1998

[51] Int. Cl.[7] ..... A01H 5/00

[52] U.S. Cl. ..... Plt./289

[58] Field of Search ..... Plt./289

[56] References Cited

U.S. PATENT DOCUMENTS

P.P. 8,803 6/1994 Fuess ..... Plt./287

*Primary Examiner*—Howard J. Locker
*Attorney, Agent, or Firm*—Christie, Parker & Hale, LLP

[57] ABSTRACT

A new plant variety of chrysanthemum producing large yellow flowers.

1 Drawing Sheet

BACKGROUND OF THE INVENTION

The present invention is directed to a new and distinct variety of chrysanthemum botanically classified as *Dendranthema grandiflora*. The varietal denomination of the new chrysanthemum is 'GOLD CREST'.

The female parent of the new variety is the variety known as 'Lynn' (U.S. Plant Pat. No. 8,171) and the male parent is the variety known as 'Empire Serenade' (U.S. Plant Pat. No. 8,803). The new variety has been asexually reproduced by vegetative cuttings in Ventura County, Calif. and the distinguishing characteristics are retained through successive generations of asexual reproduction.

SUMMARY OF THE INVENTION

'GOLD CREST' produces large, yellow decorative flowers.

COMPARISON WITH PARENTS

'GOLD CREST' differs from the female and male parents in having yellow flowers whereas 'Lynn' produces pink flowers and 'Empire Serenade' produces coral pink flowers.

BRIEF DESCRIPTION OF ILLUSTRATION

The accompanying photograph shows a typical specimen of the plant and flowers of the new variety with colors being as nearly true as possible with illustrations of this type.

DESCRIPTION OF THE PLANT

The following description of the new variety is of specimens grown in a greenhouse in Ventura County, Calif. in the month of April. 'GOLD CREST' has not been observed under all possible environmental conditions. The phenotype may vary with variations in the environment such as temperature, light intensity, day length and cultural conditions. The color designations herein are from The Royal Horticultural Society Colour Chart except where general terms are used.

To produce a commercial product the plants may be pinched once about ten days after planting. It has been observed that longevity of individual blooms of 'GOLD CREST' is about 22 days and the response time is about 7 weeks. No growth retardant has been used on specimens described. Useful growing conditions include night temperatures of about 62°–64° F. and day temperatures of about 70°–75° F. Natural season response in Ventura County, Calif. is early September.

Plant:
- *Habit.*—Mounding herbaceous perennial.
- *Height.*—About 26 cm.
- *Number of breaks from pinch.*—About 4 to 5.
- *Length of lateral branches.*—About 22 cm.
- *Stem color.*—Near 138A.

Foliage:
- *Leaf arrangement.*—Alternate.
- *Number of leaves per lateral branch.*—12 fully expanded leaves.
- *Leaf size.*—Length: About 6 cm. Width: About 3 cm.
- *Leaf shape.*—Ovate.
- *Attachment.*—Petioled.
- *Leaf apex.*—Obtuse.
- *Base.*—Tapered.
- *Margin.*—Palmately lobed.
- *Aspect.*—Slightly recurved.
- *Surface.*—Top: Lightly pubescent. Bottom: Pubescent.

Venation: Palmately net, prominent veins on underside.
- *Color.*—Upperside: Near 146C. Underside: Near 146D.

Petiole:
- *Length.*—About 1.4 cm.
- *Color.*—Near 146C.

Color:
- *Mature leaf.*—Top: Near 137A. Bottom: Near 137C.
- *Young leaf.*—Top: Near 137B. Bottom: Near 137C.

Bloom:
- *Inflorescence form.*—Cyme.
- *Flower form.*—Decorative.
- *Number of blooms per branch.*—About 10.
- *Diameter of fully expanded bloom.*—About 5.5 cm.
- *Depth of fully expanded bloom.*—About 2.5 cm.
- *Sepal number.*—About 20. Color: Near 137A.
- *Peduncle.*—Length: Peduncle length increases moving downward on the stem, terminal and shortest peduncle length are about 2.8 cm, lateral peduncles average about 7.1 cm. Aspect: Straight. Surface: Pubescent. Color: Near 138A.

Flower Bud (when just showing color):
- *Colors.*—Near 9B.
- *Diameter.*—Near 0.7 cm.
- *Height.*—About 0.8 cm.
- *Shape.*—Slightly flattened sphere.

Ray florets:

*Number per inflorescence.*—About 115.

*Texture.*—Matte.

*Shape.*—Oblanceolate.

*Apex.*—Obtuse.

*Base.*—Tapered.

*Margin.*—Entire.

*Aspect.*—Flat.

*Length.*—About 2.5 cm.

*Width.*—About 0.9 cm.

Disc florets:

*Number per inflorescence.*—About 10.

*Texture.*—Shiny.

*Shape.*—Cylindric.

*Margin.*—Entire.

*Length.*—About 0.4 cm.

*Width.*—About 0.1 cm.

Fragrance: Faint.

Color:

*General inflorescence description.*—Bright yellow decorative.

Ray florets, top side:

*Immature.*—Near 6A.

*Mature.*—Near 6A.

*Fading.*—Near 6B.

Ray floret, under side:

*Immature.*—Near 6A.

*Mature.*—Near 6C.

*Fading.*—Near 5C.

Disc florets:

*Immature.*—Near 154A.

*Mature.*—Near 9B.

*Aging.*—Disc florets fade to near 9A.

Reproductive organs:

*Ray florets.*—Pistillate. Stigma shape: 2 branched. Stigma color: Near 12A. Style length: About 0.5 cm. Style color: Near 1D.

*Disc florets.*—Stigma shape: Linear. Stigma color: Near 2A. Style Length: About 0.3 cm. Style color: Near 2D. Stamen number: About 5. Anther length: About 0.2 cm. Pollen color: Near 12A. Pollen quantity: Moderate.

What is claimed is:

1. A new and distinct chrysanthemum plant of the variety substantially as herein shown and described.

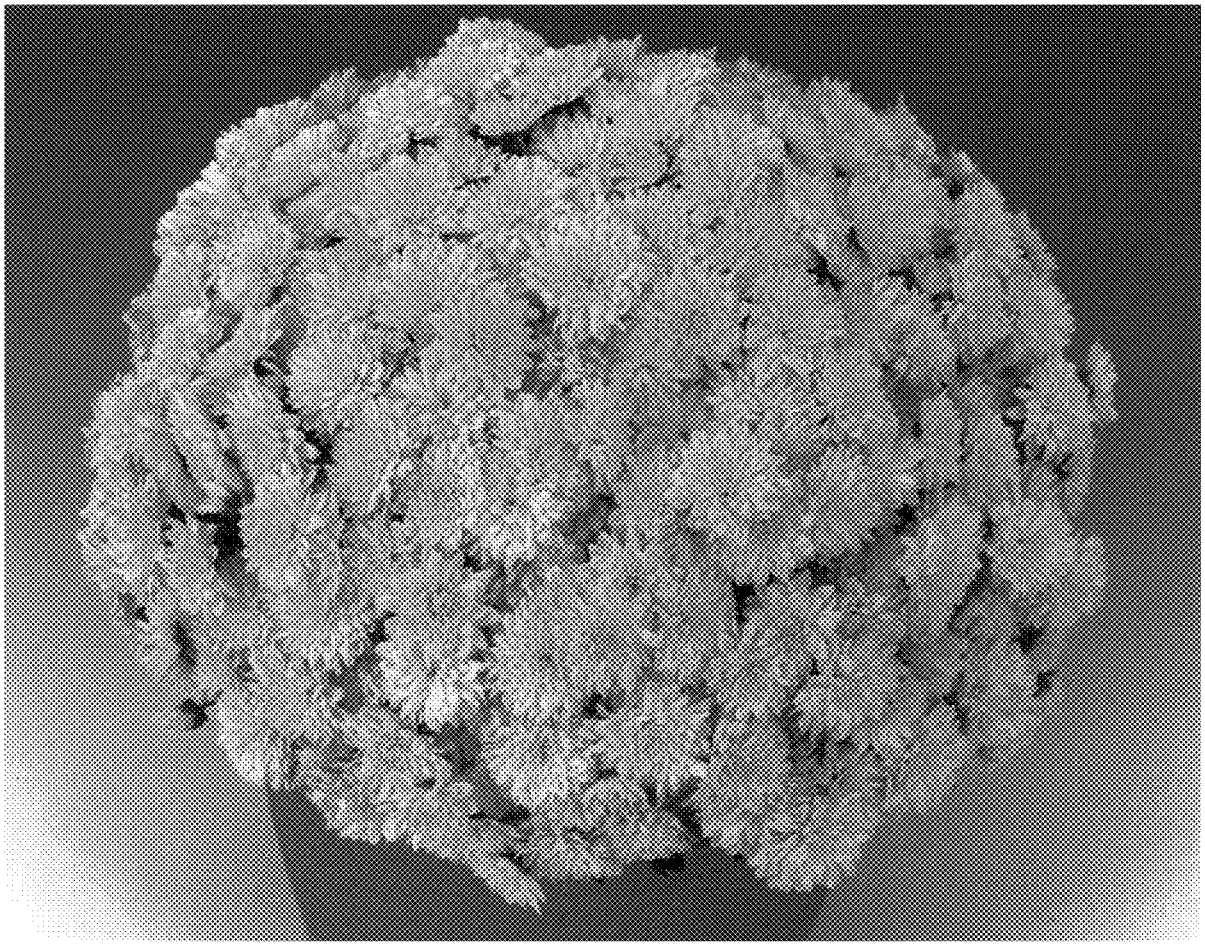

* * * * *